(12) United States Patent
Aguiyi

(10) Patent No.: US 11,576,953 B2
(45) Date of Patent: Feb. 14, 2023

(54) ANTI-VENOM VACCINE

(71) Applicant: John C. Aguiyi, Jos (NG)

(72) Inventor: John C. Aguiyi, Jos (NG)

( * ) Notice: Subject to any disclaimer, the term of this patent is extended or adjusted under 35 U.S.C. 154(b) by 133 days.

(21) Appl. No.: 16/803,953

(22) Filed: Feb. 27, 2020

(65) Prior Publication Data

US 2021/0268079 A1 Sep. 2, 2021

(51) Int. Cl.
*A61K 39/00* (2006.01)

(52) U.S. Cl.
CPC .......... *A61K 39/00* (2013.01); *A61K 2039/54* (2013.01)

(58) Field of Classification Search
None
See application file for complete search history.

(56) References Cited

PUBLICATIONS

Scire et al. Phytomedicine 18: 887-895, 2011.*
Hope-Onyekwere et al. Phytother. Res. 26: 1913-1919, 2012.*
CHEBI_63961,Feb. 21, 2012.*
Tom J.M. Molenaar, et al., "Uptake and Processing of Modified Bacteriophage M13 in Mice: Implications for Phage Display," Virology, 2002, pp. 182-191, vol. 293, Issue 1.
Susan Smith, et al., "Bedside Management Considerations in the Treatment of Pit Viper Envenomation," Journal of Emergency Nursing, 2014, pp. 537-545, vol. 40, Issue 6.
David A. Warrell, "Guidelines for the Management of Snake-Bites," World Health Organization, 2010, pp. 1-162.
Who Expert Committee on Biological Standardization, "67th Report, Annex 5: WHO Guidelines for the Production, Control and Regulation of Snake Antivenom Immunoglobulins—Replacement of Annex 2 of WHO Technical Report Series, No. 964," World Health Organization, 2018, pp. 197-388.
World Health Organization, "Report of a Consultative Meeting—Rabies and Envenomings: A Neglected Public Health Issue," World Health Organization, 2007, pp. 1-38, Geneva, Switzeriand.
James B. Mowry, et al., "2012 Annual Report of the American Association of Poison Control Centers' National position data system (NPDS): 30th annual report," Clinical Toxicology, 2012, pp. 949-1229, vol. 51, Issue 10.
Nicholas C. Kanaan, et al., "Wilderness Medical Society Practice Guidelines for the Treatment of Pitviper Envenomations in the United States and Canada," Wilderness & Environmental Medicine, 2015, pp. 472-487, vol. 26.
Debra R. Holland, et al., "The Crystal Structure of a Lysine 49 Phospholipase A2 from the Venom of the Cottonmouth Snake at 2.0-A Resolution," The Journal of Biological Chemistry, 1990, pp. 17649-17656, vol. 265, Issue 29.
Jinan Yu, et al., "[1] Affinity maturation of phage-displayed peptide ligands," Methods of Enzymology, 1996, pp. 3-27, vol. 267.
Eduardo Crosara Roncolato, et al., "Phage display as a novel promising antivenom therapy: A review," Toxicon, 2015, pp. 79-84, vol. 93.
L. Philipson, et al., "The purification and concentration of viruses by aqueous polymer phase systems," Virology, 1960, pp. 553-571, vol. 11, Issue 3.
Prakash SS, "Phage display technology for anti-venom production," Clinical Microbiology and Infection, 2015, pp. 1-3, vol. 13, Issue 4.
J. Fralick, et al., "Advances in Biological and Chemical Terrorism Countermeasures," 2008, pp. 179-202, 1st Edition, CRC Press, Boca Raton, Florida, USA.

\* cited by examiner

*Primary Examiner* — S. Devi
(74) *Attorney, Agent, or Firm* — Gearhart Law, LLC

(57) ABSTRACT

A vaccine comprising a protein immunogen capable of stimulating a protective immune response against snake venom as well as spider and bee venoms. The DNA encoding the protein is disclosed. The protein can be expressed in both recombinant host cells. The protein is useful as a thermostable, parenteral administration anti venom vaccine protective against envenomation by diverse snake species, spiders and bees.

4 Claims, 10 Drawing Sheets

Specification includes a Sequence Listing.

FLOW CHART SHOWING THE ACTIVITIES CULMINATING IN THE DEVELOPMENT OF THE ANTI-SNAKE VENOM INVENTION

Was by SDS-PAGE

The molecular weight of gpMUC is between 20-28KDa with a PI of 4.5-6

FIG. 4 gtcgactcaaactacagacDIAGRAM SHOWING SEQUENCES DNA SAMPLES

| Left Primer 1 | caccATGAGTTTGAAGAAC | | | | | | | |
|---|---|---|---|---|---|---|---|---|
| Start: 1 | Length: 19 bp | Tm: 51.7 C | GC: 42.1 % | Any: 0.0 | End: 0.0 | TB: 10.0 | HP: 0.0 | 3' Stab: 3.0 Penalty: 9.302 |
| Right Primer 1 | GTCGACTCAAACTACAGAC | | | | | | | |
| Start: 988 | Length: 19 bp | Tm: 52.8 C | GC: 47.4 % | Any: 8.7 | End: 0.0 | TB: 7.0 | HP: 0.0 | 3' Stab: 3.5 Penalty: 8.159 |
| Pair: | Product Size: 988 bp | | | Any: 8.7 | End: 0.0 | TB: 16.0 | | Penalty: 17.460 |

```
  1  caccATGAGT  TTGAAGAACA  ACATGGTGGT  GCTAAAGGTG  TGTTTGTTGC
 51  TTCTTTTCCT  TGTGGGGGTT  ACAGCTGCAC  GCATGGAACT  GAGCTTCTTC
101  AAAAGTGATC  AGTCATCAAG  TTATGATGAT  GATGAGTATT  CAAAACCATG
151  CTGTGATCTC  TGCATGTGCA  CACGCTCAAT  GCCTCCTCAA  TGCAGCTGTG
201  AAGATATTAG  GCTGAATTCA  TGCCACTCAG  ATTGTAAGAG  CTGTATGTGC
251  ACACGCTCAC  AGCCAGGACA  GTGTCGTTGT  CTTGACACCA  ACGACTTCTG
301  CTACAAACCT  TGCAAGTCCA  GAGATGACTA  GATGAAGCCA  GTGCTACTTC
351  TTACACTCTC  CTTCCTCCCC  CTCTTTGCTT  TCTTAACTAA  CCTTCCATTA
401  GCTTTCTCAA  ATGAAGTTGA  ACAAGTTGTG  GATACCAAAG  GCAAGCCCAT
451  TTTCCCTGGT  GCTACATACT  ACATTATGCC  AGCATTATTT  GGGGCAGCTG
501  GTGGTGGAGT  GAAACTTGGC  AAGACTGCAA  ACTCAAGGTG  CCCAGTTACT
551  GTTTTGCAAG  ACTTTTCAGA  AGTGGTTCGT  GGTCTTCCAG  TGAGATTCAA
601  GATACCTGGA  ATAAGCCCTG  GCATCATCTT  TACAGGTACC  CCACTGGAAA
651  TTGAGTTTGC  ATGGAAGCCA  GGGTGTGCTG  AATCCTCGAA  ATGGGTGGTG
701  TTTGTGGACA  ATGAAATTGA  AAAGGCATGT  GTGGGAATTG  GTGGTCCTGA
751  AGATCATCCA  GGGCAACAAA  CCCGTAGTGG  CACATTCCAC  ATTGAGAAAT
801  ACAATTTTGG  ATATAAGCTT  GTGTTTTGTA  TCAATGGCTC  TTCCGTTTGT
851  TTGGATATTG  GGAGGTTTGA  TGCTAACAAT  GGTGAGAGTG  GAAGACGGTT
901  GAATCTCACT  GAGCATGAGG  CCTTCGACCT  TGTTTTCGTA  GAGGCTTCTG
951  ACTATGAAGA  AATAATTAAG  TCTGTAGTTT  GAGTCGAC
```

1% Agarose gel image showing restriction digest result of pESC vector with cloned double contig fragment of approximately 990 bp

FIG. 7A

```
Phaseolus acutifolius    ATGATGGTGCTGAAGGTGTGTCTGTTACTAGTTTTCCTTGCAGGGGTTACTACTGCTCGC  60
Phaseolus grayanus       ATGATGGTGCTGAAGGTGTGTTTGTTGCTAGTTTTTCTTGTAGGGGTTACTACTGCTCGC  60
Phaseolus maculatus      ATGATGGTGCTGAAGGTGTGTCTGTTACTAGTTTTCCTTGCAGGGGTTACTACTGCTCGC  60

Phaseolus acutifolius    ATGGATCTGAACCACCTCATCAGAAGTAATCATCATGACTCAAGCGATGAGCCTTCTGAG  120
Phaseolus grayanus       ATGGATCTGAACCACCTCATCAGAGGTAATCATCATGACTCAAGCGATGAGCCTTCTGAG  120
Phaseolus maculatus      ATGGATCTGAACCACCTCATCAGAAGTAATCATCATGACTCAAGCGATGAGCCTTCTGAG  120

Phaseolus acutifolius    TCTTCAGAACCATGCTGTGATCACTGCATATGCACAGCTTCAATACCTCCTATATGCCAA  180
Phaseolus grayanus       TCTTCAGAACCATGCTGTGATCTCTGCGTGTGCACAGATTCAATACCTCCTATATGCCAA  180
Phaseolus maculatus      TCTTCAGAACCATGCTGTGATCTCTGCTTGTGCACAGCTTCAATACCTCCTATATGCCAA  180

Phaseolus acutifolius    TGCACAGATATTAGGTTGAATTCATGCCACTCAGCTTGCAAATCCTGTATGTGTACGCGA  240
Phaseolus grayanus       TGCACAGATATTAGGTTGAACTCATGCCACTCAGCTTGCAAAACCTGTATGTGTACACGA  240
Phaseolus maculatus      TGCTCAGATATTAGGTTGAATTCGTGCCACTCAGCTTGCAAATCCTGTATGTGTACACGA  240

Phaseolus acutifolius    TCAATGCCAGGCAAGTGTCGTTGCCTTGACACCACTGATTTTTGTTACAAATCTTGCAAG  300
Phaseolus grayanus       TCAATGCCAGGCAAGTGTCGTTGCCTTGACACCACTGATTTTTGTTACAAATCTTGCAAG  300
Phaseolus maculatus      TCAATGCCAGGCAAGTGTCGTTGCCTTGACACCACCGATTTCTGTTACAAATCTTGCAAG  300
Phaseolus microcarpus    ----------------TGTCGTTGCCTTGACACCACCGATTTCTGTTACAAATCTTGCAAG  45
Glycine max              ----------------TGTCGTTGCCTTGACACCACCGACTTCTGCTACAAACCTTGCAAG  45
                                         ********** ** ** ** ****** *******

Phaseolus acutifolius    TCCAGTGGTGAAGATGATGACTGA 324
Phaseolus grayanus       TCCAGTGGTGAAGATGATGACTGA 324
Phaseolus maculatus      TCCAGTGGTGAAGATGATGACTGA 324
Phaseolus microcarpus    TCCAGTGGTGAAGAT--------- 60
Glycine max              TCCAGTGATGAAGAT--------- 60
                         ******* *******
```

FIG. 7B

PREDICTED DNA SEQUENCE OF PART OF THE PROTEIN ON THE BASIS
OF THE ALIGNMENT IN FIG 7A

```
TGT CGT TGC GTT GAC ACC ACC/T GAT TTT/C TGT TAC AAA CCT TGC
 C   R   C   V   D   T   T     D   F     C   Y   K   P   C

AAG TCC GGT GGT GGA GAT
 K   S   G   G   G   D
```

FIG. 9

GTTTTCGTAGAGGCTTCTGACTATGAAGAAATAATTAAGTCTGTAGTTTGAGTCGACGG
ATCCATGAGTTTGAAGAACAACATGGTGGTGCTAAAGGTGTGTTTGTTGCTTCTTTTCC
TTGTGGGGGTTACAGCTGCACGCATGGAACTGAGCTTCTTCAAAAGTGATCAGTCATCA
AGTTATGATGATGATGAGTATTCAAAACCATGCTGTGATCTCTGCATGTGCACACGCTC
AATGCCTCCTCAATGCAGCTGTGAAGATATTAGGCTGAATTCATGCCACTCAGATTGTA
AGAGCTGTATGTGCACACGCTCACAGCCAGGACAGTGTCGTTGTCTTGACACCAACGAC
TTCTGCTACAAACCTTGCAAGTCCAGAGATGACTAGATGAAGCCAGTGCTACTTCTTAC
ACTCTCCTTCCTCCCCTCTTTGCTTTCTTAACTAACCTTCCATTAGCTTTCTCAAATG
AAGTTGAACAAGTTGTGGATACCAAAGGCAAGCCCATTTTCCCTGGTGCTACATACTAC
ATTATGCCAGCATTATTTGGGGCAGCTGGTGGTGGAGTGAAACTTGGCAAGACTGCAAA
CTCAAGGTGCCCAGTTACTGTTTTGCAAGACTTTTCAGAAGTGGTTCGTGGTCTTCCAG
TGAGATTCAAGATACCTGGAATAAGCCCTGGCATCATCTTTACAGGTACCCACTGGAA
ATTGAGTTTGCATGGAAGCCAGGGTGTGCTGAATCCTCGAAATGGGTGGTGTTTGTGGA
CAATGAAATTGAAAGGCATGTGTGGGAATTGGTGGTCCTGAAGATCATCCAGGGCAAC
AAACCCGTAGTGGCACATTCCACATTGAGAAATACAATTTTGGATATAAGCTTGTGTTT
TGTATCAATGGCTCTTCCGTTTGTTTGGATATTGGGAGGTTTGATGCTAACAATGGTGA
GAGTGGAAGACGGTTGAATCTCACTGAGCATGAGGCCTTCGACCTT

ANTI-VENOM VACCINE

CLAIM OF PRIORITY

This application claims no priority to any patent or patent application.

FIELD OF THE EMBODIMENTS

Embodiments of the disclosure are related at least to the fields of biology, molecular biology, immunology, medicine and vaccines. In specific embodiments the disclosure relates to a vaccine against envenomation, isolated DNA encoding an immunogenic protein, and an immunogenic protein useful in the production of a vaccine.

BACKGROUND OF THE EMBODIMENTS

Treatment for envenomation is largely through the administration of anti-venom. The anti-venom in current use generally is available in two forms, namely the polyvalent and monovalent, which are obtained by injecting snake venoms into horses and obtaining anti-bodies generated by the horse for further processing. Both forms are currently expensive and generally above the means of people in remote, austere or impoverished areas where envenomation is a danger.

Antibody-based antivenoms are developed by exposing host animals to pure venom for immunological conditioning and extracting the resulting antibodies. While an antibody-based strategy has yielded successful therapies for some snake species, there remain limitations in safety, efficacy, and the high cost of manufacturing. Additionally, antibody-based strategies have limited effectiveness in combating envenomation from other animals such as arachnids and medusae.

Serum is then isolated from the animals, and venom-reactive antibodies purified. While this antibody-based strategy has yielded successful therapies for some snake species, there remain limitations in safety, efficacy, and the economic aspects of manufacturing. One of the most serious side effects of antibody-based antivenom is patient's immunological reactions against heterologous immunoglobulins from horses or sheep, known as serum sickness. In addition, most antibody-based solutions require either special storage conditions or, if lyophilized, reconstitution prior to administration; both of which diminish their utility in remote and austere conditions. Although others have produced antibody-based antivenoms, their continued pursuit of anti-venom production is questionable given the impact of a costly and time-consuming production process, as well as limitations of application.

The following references provide background information on the state of the art in antivenom technology and are herein incorporated by reference in their entireties: Molenaar, T. J. et al. Uptake and processing of modified bacteriophage M13 in mice: implications for phage display. Virology 293, 182-191, doi:10.1006/viro.2001.1254 (2002); Rabies and Envenomings A Neglected Public Health Issue (WHO 2007); WHO Guidelines for the Production Control and Regulation of Snake Antivenom Immunoglobulins (WHO 2010); Warrell, D. A. Guidelines for the management of snake-bites (WHO 2010); Smith, S. et al. Bedside management considerations in the treatment of pit viper envenomation. J Emerg Nurs 40, 537-545, doi:10.1016/j.jen.2014.01.002 (2014); Mowry, J. B., Spyker, D. A., Cantilena, L. R., Jr., Bailey, J. E. & Ford, M. 2012 Annual Report of the American Association of Poison Control Centers' National Poison Data System (NPDS): 30th Annual Report. Clin Toxicol (Phila) 51, 949-1229, doi:10.3109/15563650.2013.863906 (2013); Kanaan, N.C. et al. Wilderness Medical Society Practice Guidelines for the Treatment of Pitviper Envenomations in the United States and Canada. Wilderness Environ Med 26, 472-487, doi:10.1016/j.wem.2015.05.007 (2015); Holland, D. R. et al. The crystal structure of a lysine 49 phospholipase A2 from the venom of the cottonmouth snake at 2.0-A resolution. J Biol Chem 265, 17649-17656 (1990); Fralick, J., Chadha-Mohanty, P. & Li, G. in Advances in Biological and Chemical Terrorism Countermeasures (eds R. Kendall, S. Presley, G. Austin, & P. Smith) 179-202 (CRC Press, 2008); Philipson, L., Albertsson, P. A., Frick, G. The purification and concentration of viruses by aqueous polymer phase systems. Virology, 11, 553-571 (1960); Yu, J. & Smith, G. P. [1] Affinity maturation of phage-displayed peptide ligands. 267, 3-27, doi: 10.1016/s0076-6879(96)67003-7 (1996); Prakash S.S. Phage display technology for anti-venom production. Clinical Microbiology and Infection 13:4 (October 2015); Roncolato, E. C. et al. Phage display as a novel promising antivenom therapy: a review. 93:79-84 Toxicon. (January 2015; Epub November 2014).

SUMMARY OF THE EMBODIMENTS

The present invention provides an anti-venom vaccine against a multitude of snake venoms as well as venoms of spiders and bees. The vaccine is thermostable and inexpensive to manufacture. The vaccine thereby addresses problems which make the use of conventional antivenoms difficult or impossible in remote, austere and impoverished areas of the world.

An aspect of the present invention is an isolated DNA sequence of SEQ ID NO. 1 encoding an immunogenic protein. The DNA sequence is isolated from *Mucuna pruriense*. Embodiments of this aspect include cloning vectors carrying some or all of the isolated DNA of SEQ ID NO. 1. The cloning vectors may be any vector useful for propagating the DNA or expressing the protein encoded by the DNA. Particular embodiments include expression vectors for the expression of the polypeptide encoded by the DNA of SEQ ID NO. 1.

Another aspect of the present invention includes recombinant host cells carrying the DNA of SEQ ID No 1. Embodiments of this aspect include recombinant prokaryotic and eukaryotic host cells. Particular embodiments include *Escherichia coli* host cells and yeast host cells. Another aspect of the present invention are recombinant host cells carrying the DNA of SEQ ID NO. 1 in an expression vector. Embodiments of this aspect include recombinant vectors having promoters positioned to drive expression of the protein encoded by the DNA of SEQ ID NO. 1. Promoters can be constitutive and express the protein at a regular rate or be inducible and be caused to express the protein at a particular time. Embodiments of this aspect include cells that express or overexpress the protein encoded by the DNA of SEQ ID NO. 1.

Another aspect of the present invention includes isolated and purified protein, portions of the protein or peptides encoded by SEQ ID NO. 1. Embodiments of this aspect include the entire protein encoded by SEQ ID NO. 1, immunogenic portions of the protein or immunogenic peptides derived from the protein. Preferred embodiments include immunogenic peptides of at least 5 amino acids in length and 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length.

Another aspect of the invention is a vaccine useful against the effects of envenomation by a variety of snakes, spiders and bees. Embodiments of this aspect include vaccines comprising adjuvants. Embodiments of this aspect include the entire protein encoded by the DNA of SEQ ID NO. 1. Embodiments of this aspect can include immunogenic portions of a peptide or multiple peptides derived from the protein encoded by the DNA of SEQ ID NO. 1. Embodiments of this aspect are thermostable vaccines capable of withstanding temperatures up to 50° C. and that do not require cold chain transportation for distribution. In particular embodiments the vaccines have a PH range of about 4.6 to 8 which is considered conducive.

In some vaccine embodiments, the peptide or polypeptides disclosed herein are formulated with a range of alternate delivery systems such as nanoparticles. In some embodiments, a composition comprising a nanoparticle and a peptide or polypeptide disclosed herein are provided. In some embodiments, the present disclosure provides an aqueous liposome nanoparticle composition comprising an aqueous dispersion of liposome nanoparticles and a peptide or polypeptide disclosed herein. In some embodiments, the nanoparticles encapsulate a peptide or polypeptide disclosed herein. In some embodiments, a peptide or polypeptide disclosed herein is added to a pre-formed liposome composition. In other embodiments, a peptide or polypeptide disclosed herein is incorporated in the liposomes during the formation of the liposomes.

Also provided herein are vaccine compositions comprising a peptide or polypeptide described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide or polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrin; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical vaccine compositions comprise a peptide or polypeptide described herein, and optionally one or more additional prophylactic or therapeutic agents, in a pharmaceutically acceptable carrier. In a specific embodiment, pharmaceutical compositions comprise an effective amount of a peptide or polypeptide described herein, and optionally one or more additional prophylactic of therapeutic agents, in a pharmaceutically acceptable carrier. In some embodiments, the peptide or polypeptide is the only active ingredient included in the pharmaceutical composition.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurial, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethyl cellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition can be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Preparations for parenteral administration of composition comprising a peptide or polypeptide disclosed herein include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

BRIEF DESCRIPTION OF THE DRAWINGS

FIG. 4 shows primer strategy. Left Primer is SEQ ID NO: 2. Right Primer is SEQ ID NO: 3. The 951 nt sequence is SEQ ID NO: 4.

FIG. 7A shows sequence alignments. *Phaseoulus acutifolius* SED ID NO: 5. *Phaseoulus grayanus* SEQ ID NO: 6. *Phaseoulus maculatus* SEQ ID NO: 7. *Phaseoulus microcarpus* SEQ ID NO: 8. *Glycine max* SEQ ID NO: 9.

FIG. 7B shows predicted DNA sequences based on alignments. DNA sequence SEQ ID NO: 10. Protein sequence SEQ ID NO: 11.

FIG. 9 shows SEQ ID NO: 1.

DETAILED DESCRIPTION OF THE EMBODIMENTS

Figure 1:
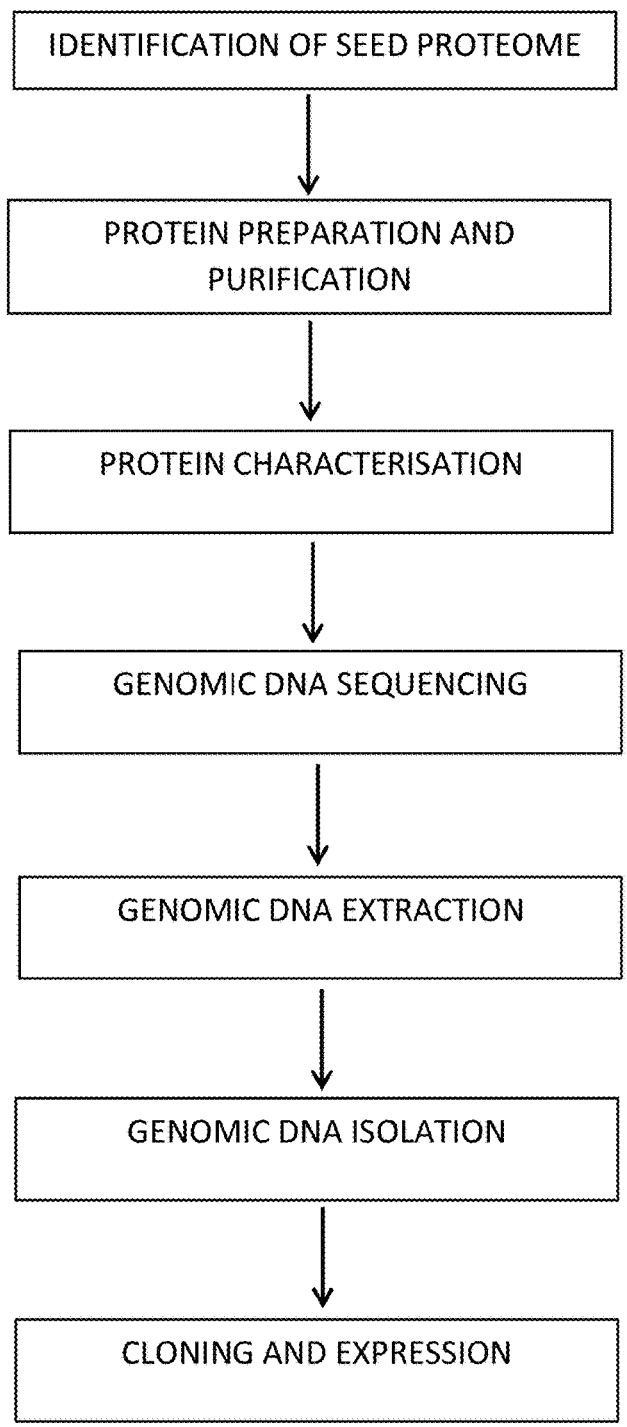
FIG. 1 shows a flow chart of the overall procedure.

Seeds of *Mucuna pruriense* were identified as potentially having properties of protecting humans from envenomation. Study was undertaken to identify an active agent that could afford protection against envenomation. The overall process is outlined in FIG. 1.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

A "phage" or "bacteriophage" refers to a virus that infects bacteria. The term "phage" is used to refer to both types of viruses but in certain instances as indicated by the context may also be used as shorthand to refer to a bacteriophage specifically. Bacteriophage are obligate intracellular parasites that multiply inside bacteria by making use of some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid may be either DNA or RNA but not both and it can exist in various forms. Phages have two means by which to infect bacterial cells. One is lysogeny, in which the phage DNA incorporates into the chromosome of the bacterium and becomes dormant for many generations. At least one environmental inducer is required to cause the phage DNA to excise from the bacterial chromosome and establish the second type of infection, the lytic phase. In this phase, the bacterium is transformed into a phage-making factory. Hundreds of phages are produced, and the bacterial cell is lysed to release them. The released phage then finds another host bacterium, and the process repeats.

"Antivenom" is a serum which acts against the effects of venom. Antivenom is used to treat certain venomous bites and stings. In one particular embodiment herein, antivenom is used to treat a snake bite. Specific antivenom needed depends on the species involved. "Universal antivenom reacts with venom or proteins of venom of more than one species. Said another way, Universal antivenom is antivenom that cross-reacts with venoms of different species.

"Phage display panning" is a technique to examine protein-protein, protein-peptide, and protein-DNA interactions using bacteriophages. Phage displace panning allows for enrichment of relevant phage.

A "consensus sequence" is a sequence of nucleotides or amino acids in common between regions of homology in different but related DNA or RNA or protein sequences.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

A "peptide" derived from a polypeptide refers to a chain comprising at least two consecutively linked amino acid residues of a length that is shorter that the full length of the polypeptide.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation (Mei et al., Blood 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination.

As used herein, an "amino acid corresponding to," "site corresponding to," or "equivalent amino acid" in a protein sequence is identified by alignment to maximize the identity or similarity between a first protein sequence and a second protein sequence. The number used to identify an equivalent amino acid in a second protein sequence is based on the number used to identify the corresponding amino acid in the first protein sequence.

The term "expression" as used herein refers to a process by which a polynucleotide produces a gene product, for example, an RNA or a polypeptide.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Methods of identifying nucleotide and amino acid conservative substitutions which do not eliminate antigen binding are well-known in the art (see, e.g., Brummell et al., Biochem. 32: 1180-1187 (1993); Kobayashi et al. Protein Eng. 12(10):879-884 (1999); and Burks et al. Proc. Natl. Acad. Sci. USA 94:412-417 (1997)). For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a peptides disclosed herein can be replaced with an amino acid residue with a similar side chain.

As used herein, an "epitope" is a term in the art and refers to a localized region of an antigen to which a peptide can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an peptide disclosed herein binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303).

The term "nucleic acid molecule," as used herein, is intended to include DNA molecules and RNA molecules. A nucleic acid molecule can be single-stranded or double-stranded and can be cDNA.

The term "downstream" refers to a nucleotide sequence that is located 3' to a reference nucleotide sequence. "Downstream" can also refer to a peptide sequence that is located C-terminal to a reference peptide sequence.

The term "upstream" refers to a nucleotide sequence that is located 5' to a reference nucleotide sequence. "upstream" can also refer to a peptide sequence that is located N-terminal to a reference peptide sequence.

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence. A polynucleotide, which encodes a gene product, e.g., a polypeptide, can include a promoter and/or other transcription or translation control elements operably associated with one or more coding regions. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions, which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "percent sequence identity," "percent identity," "sequence identity," or "identity" are used interchangeably and refers to the number of identical matched positions shared between two polynucleotide or polypeptide sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The comparison of sequences and determination of percent identity between two sequences can be accomplished using a mathematical algorithm, as described in the non-limiting examples below.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (Madison, Wis.), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to the nucleic acid molecules described herein. BLAST protein searches can be performed with the XBLAST program, score=50, word length=3 to obtain amino acid sequences homologous to the protein molecules described herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein. Exemplary host cells include, but are not limited to, prokaryotic cells (e.g., *E. coli*), or alternatively, eukaryotic cells, for example, fungal cells (e.g., yeast cells such as *Saccharomyces cerevisiae, Pichia pastoris*, or *Schizosaccharomyces pombe*), and various animal cells, such as insect cells (e.g., Sf-9) or mammalian cells (e.g., HEK293F, CHO, COS-7, NIH-3T3).

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which a heterologous moiety (e.g., a half-life extending moiety) is inserted between two adjacent amino acids.

"Treat," "treatment," or "treating," as used herein refers to, e.g., the reduction in severity of a disease or condition; the reduction in the duration of a condition course; the amelioration or elimination of one or more symptoms associated with a disease or condition; the provision of beneficial effects to a subject with a disease or condition, without necessarily curing the disease or condition.

As used herein, "administering" refers to the physical introduction of a composition comprising a therapeutic agent to a subject, using any of the various methods and delivery systems known to those skilled in the art. Different routes of administration for peptides described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, a peptide described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

By "vaccine" is intended a composition useful for stimulating a specific immune response (or immunogenic response) in a subject. In some embodiments, the immunogenic response is protective or provides protective immunity. For example, in the case of a disease-causing organism the vaccine enables the subject to better resist infection with or disease progression from the organism against which the vaccine is directed. Alternatively, in the case of a cancer, the vaccine strengthens the subject's natural defenses against cancers that have already developed. These types of vaccines may also prevent the further growth of existing cancers, prevent the recurrence of treated cancers, and/or eliminate cancer cells not killed by prior treatments.

As used herein, the term "effective amount" in the context of the administration of a therapy to a subject refers to the amount of a therapy that achieves a desired prophylactic or therapeutic effect.

As used herein, the terms "subject" and "patient" are used interchangeably. The subject can be an animal. In some embodiments, the subject is a mammal such as a non-primate (e.g., cow, pig, horse, cat, dog, rat, etc.) or a primate (e.g., monkey or human), most preferably a human. In certain embodiments, such terms refer to a non-human animal (e.g., a non-human animal such as a pig, horse, cow, cat or dog). In some embodiments, such terms refer to a pet or farm animal. In specific embodiments, such terms refer to a human.

As used herein, the terms "ug" and "uM" are used interchangeably with "µg" and "µM," respectively.

Vaccines of the present invention are compositions comprising the gpMuc protein or at least one immunogenic peptide derived from the gpMuc protein or a combination of the above. The gpMuc polypeptides are thermostable allowing the vaccines the be distributed without the need for a cold chain distribution system. Vaccines of the present invention can be adjuvanted with adjuvants known to those of skill in the art. Adjuvants may enhance the immunogenicity of the vaccine. Vaccines of the present invention may contain preservatives. The vaccines may be in liquid form or may be lyophilized and reconstituted before administration. Vaccines of the present invention can be used in the treatment of human patients and in livestock.

Vaccines of the present invention also include fusion protein immunogens wherein at least one peptide of the immunogen encoded by SEQ ID NO. 1 are fused to a carrier protein. Fusion proteins are made by fusing the nucleic acid sequences encoding the carrier protein and the peptide and expressing the fused protein as a single polypeptide. Fusion proteins are useful to present small peptide immunogens to the immune system and elicit an immune response.

Vaccines of the present invention also include conjugate vaccines wherein at least one peptide of the immunogen encoded by SEQ ID NO. 1 is conjugated to a carrier protein.

Conjugate vaccines are useful to present small peptide immunogens to the immune system and elicit an immune response The practice of the invention employs, unless otherwise indicated, conventional molecular biological and immunological techniques within the skill of the art. Such techniques are well known to the skilled worker and are explained fully in the literature. See, e.g., Bailey, J. E. and Ollis, D. F., Biochemical Engineering Fundamentals, McGraw-Hill Book Company, N Y, 1986; Current Protocols in Immunology, John Wiley & Sons, Inc., NY, N.Y. (1991-2015), including all supplements; Current Protocols in Molecular Biology, John Wiley & Sons, Inc., NY, N.Y. (1987-2015), including all supplements; Sambrook, et al., Molecular Cloning: A Laboratory Manual, 2nd Edition, Cold Spring Harbor, N.Y. (1989); and Harlow and Lane, Antibodies, a Laboratory Manual, Cold Spring Harbor, N.Y. (1989), all the contents of which are incorporated by reference herein in their entireties.

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the packaging vectors, cell lines and/or methods of the invention may be made without departing from the spirit of the invention and the scope of the appended claims.

Example 1

Isolation of Seed Proteome
Seeds Mucuna pruriense were ground into fine powder dissolved in 500 ml $H_2O$. The supernatant was subject to ammonium sulphate precipitation of protein. The pellet obtained after centrifugation was resuspended in 50 ml phosphate buffer and analysed by 12% SDS-Page.
Protein Preparation and Purification
The protein was produced through recombinant DNA technology. A water extract of the seed was subjected to precipitation with solid $(NH_4)_2SO_4$ 80% and components separated by gel filtration on SEPHADEX G50 column obtaining two fractions, one proteic and non-proteic.
Protein Characterisation
Proteins were determined with Bio-Rad protein reagent using crystalline bovine serum albumin as standard at all steps. The protein, a multiform glycoprotein (gpMuc) was purified using concanavalin A affinity chromatography and using 2-D gel electrophoresis separated into seven isoforms having molecular weights in the range of 20.3 to 28.7 KDa and pH from 4.8-6.5 and thermostable at 50° C. The gpMuc protein of interest was sequenced by Edman degradation to establish the internal sequence DDREPV-DT (SEQ ID NO: 12) and the C-terminal was determined based on homologous sequences available in the data bank. N-terminal sequences show consensus sequence DDREPV-DT (SEQ ID NO: 12) found in soybean kunitz-type inhibitor. The gpMuc contains both N- and O-glycans. The glycan is involved in the antigenicity of gpMuc. The internal sequence also showed sequences highly similar to consensus sequences found in mung bean, soybean Bowman like type inhibitor, of molecular weight range of 8-16,000 KDa. The gpMuc protein inhibited proteases when assessed using trypsin and chymotrypsin.

Example 2

Figure 8:
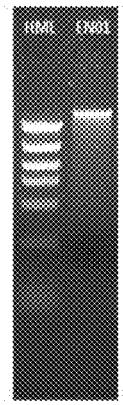
FIG. 8 shows analysis of a plasmid vector used herein.

Genomic DNA Analysis
The DNA sequences and predicted amino acids sequences are compared with the sequence from the GENBANK database using BLAST program. The alignment is performed using the online CLUSTER program.
Genomic DNA Extraction
CTAB method was used to isolate genomic DNA with high purity that was subsequently sequenced using epitopes mapped out from whole Genome, which was used in preparing a clone using plasmids purchased from Genwiz. (FIG. 8).
Genomic DNA Isolation
Genomic DNA isolated from the seed and was digested with restriction endonucleases enzymes. The DNA was digested and resolved by electrophoresis on 1% agarose gel.

Example 3

Figure 6:
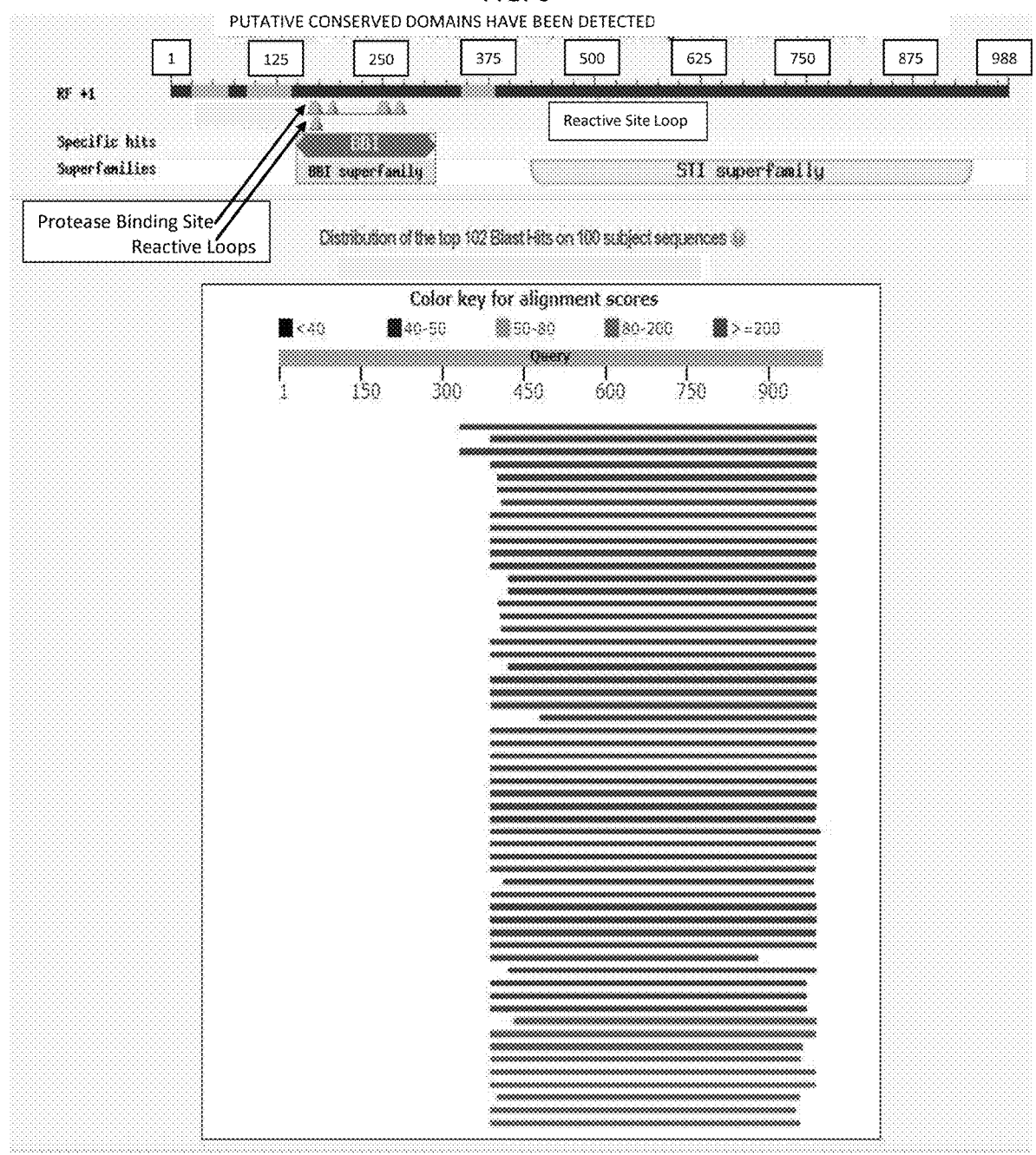
FIG. 6 shows an alignment of conserved sequences.

Conserved domain searches were carried out in order to analyse sequence similarities against the non-reductant protein sequences (nr) database. See FIG. 6 for translated nucleotide (blastx) results. Translated blastx search results with majority of alignment scores>=200 with percent identity of approximately 72-1000%. The putative conserved domains representing sequence homology between our query and the protein database were analysed to help with bioinformatic analysis.

The target sequence was then amplified for cloning and expression. Primers were designed as shown in FIG. 4 and the DNA was amplified by standard methods.

Example 4

Figure 5:
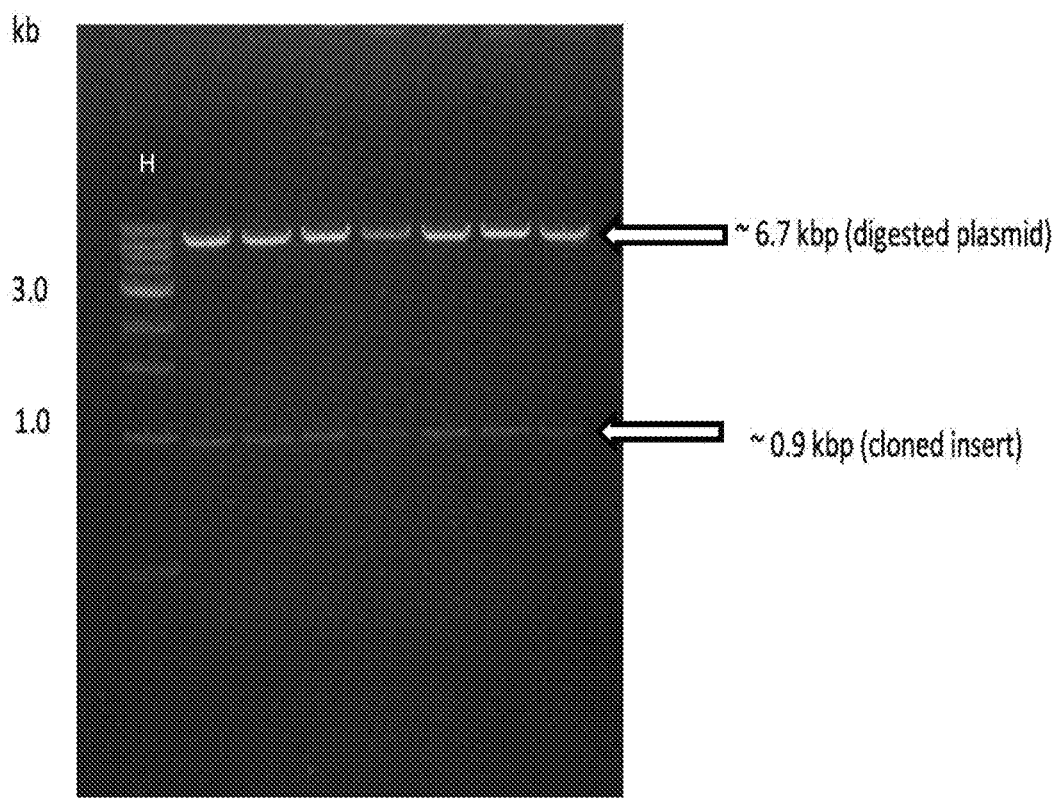
FIG. 5 shows an agarose gel demonstrating the approximately 990 bp cloned DNA.

Cloning
Primers have also been designed with recognition sequences for the gateway entry vector (pENTR/SD/D-TOPO) which aid in the generation of an entry clone. The entry clone was used in an LR reaction and the product was transferred into an expression vector (pET-3a) where expression in E. coli BL21 DE3 cells (Invitrogen, United Kingdom) was carried out. The approximately 990 bp cloned double contig fragment is shown excised by restriction digest of a pESC vector and run on an agarose gel in FIG. 5.

Example 5

Figure 2:
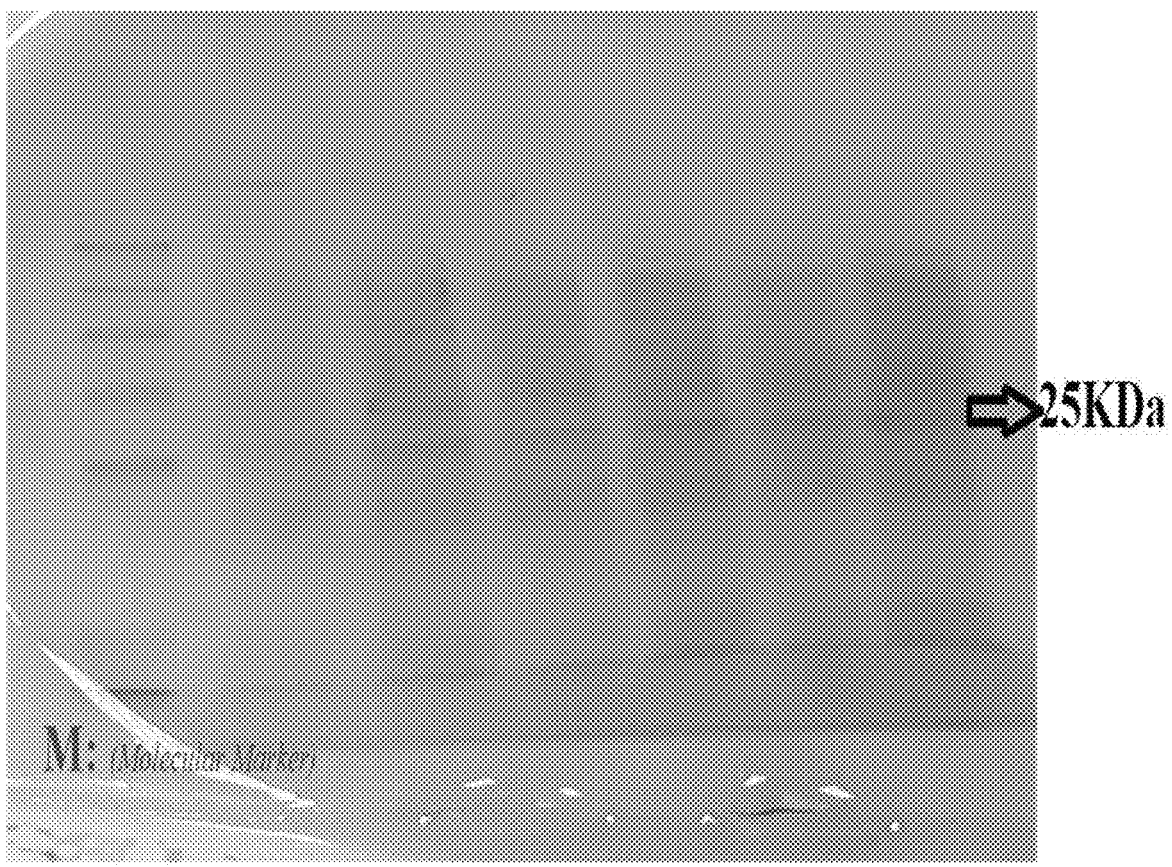
FIG. 2 shows SDS-PAGE gel of expressed protein.
Figure 3:
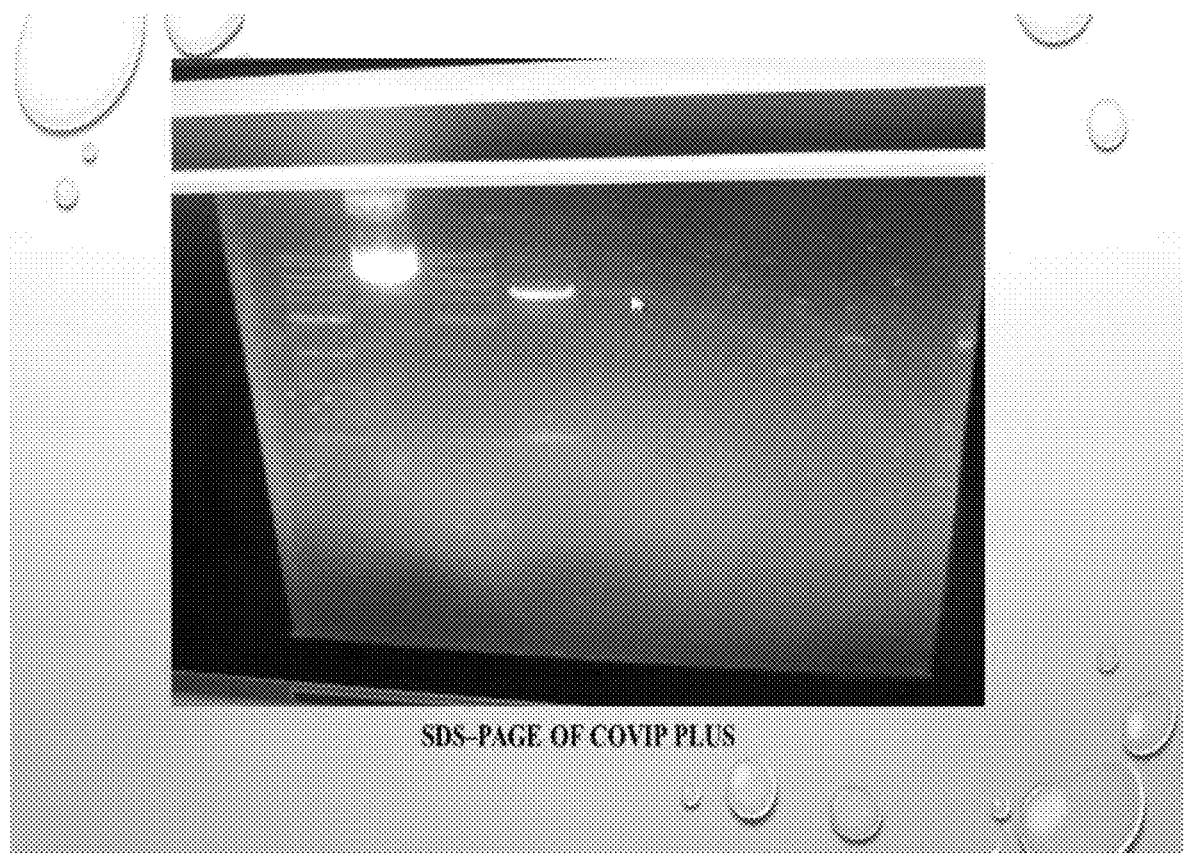
FIG. 3 shows SDS-PAGE gel of purified gpMuc protein.

Expression
Genes encoding gpMuc protein sub-unit were cloned into PET 28a vectors with N-terminal or internal terminal and a combination or fusion of the two. The clones were transformed into standard E. coli BL21 (DE3) cells for expression. Cultures were grown in LB at 37° C. to an OD 600 of 0.5-0.7 and induced for 3 hours with IMIPTG. Cells were pelleted and lysed directly in SDS-PAGE loading buffer and analysed by gel electrophoresis. The gel was stained with COOMASIE BLUE dye. (FIG. 2) Clear lysate was loaded onto Ni-NTA SEPHAROSE gel. The molecular weight of gpMUC is between 20-28 KDa with a PI of 4.5-6. (FIG. 3). Large scale protein purification can be accomplished by chromatography Con A affinity tandem anionic-cationic exchange and gel filtration. Larger scale production of the gpMuc protein was performed. BL21(DE3) E. coli cells were transformed with an expression vector encoding gpMuc and selected by antibiotic resistance. Protein expression was conducted in cultured cells expanded in LB broth and induced with IPTG using standard methodologies known in the art. Cells were collected, washed and lysed in 25 mM TRIS-Cl, 2 mM EDTA, pH 7.6 with lysozyme and optionally protease inhibitors. Cellular debris was cleared by centrifugation and the gpMuc protein was isolated from the supernatant.

Example 6

The gpMuc protein is injected into animals. Mice, rabbits, sheep and other animals may be used in testing. After 30 days plasma in harvested. The plasma is tested for immunological activity with snake venom. IgG and Ig M antibodies are produced.

Example 7

The gpMuc protein is used to formulate a vaccine. An effective amount of the gpMuc protein, an immunogenic peptide thereof, a gpMuc peptide fused to a carrier protein or a gpMuc peptide conjugated to a carrier protein and optionally an adjuvant are formulated in a pharmaceutically acceptable carrier and packaged for use. The vaccine may be liquid or lyophilized for reconstitution before administration. The vaccine is administered to a patient in need thereof.

This application incorporates the Sequence Listing having the filename 16803953_Seq_Listing_updated20220922_ST25.txt, created Sep. 22, 2022, with a file size of 6,009 bytes and having been filed in the United States Patent Office via EFS-Web on Sep. 22, 2022.

What is claimed:

1. An immunogenic composition comprising an effective amount of an isolated multiform glycoprotein (gpMuc) in a pharmaceutically acceptable carrier, wherein the gpMuc is encoded by SEQ ID NO: 1.

2. The composition of claim 1 wherein the composition is thermostable up to 50° C.

3. The composition of claim 1 wherein the composition is formulated for parenteral administration vaccine with a pH of 4.6-6.5.

4. An isolated and purified polypeptide encoded by SEQ ID NO: 1, wherein the polypeptide comprises a full-length polypeptide encoded by SEQ ID NO: 1.

* * * * *

SEQUENCE LISTING

```
<160> NUMBER OF SEQ ID NOS: 12

<210> SEQ ID NO 1
<211> LENGTH: 990
<212> TYPE: DNA
<213> ORGANISM: Mucuna pruriense

<400> SEQUENCE: 1
gttttcgtag aggcttctga ctatgaagaa ataattaagt ctgtagtttg agtcgacgga      60
tccatgagtt tgaagaacaa catggtggtg ctaaaggtgt gtttgttgct tcttttcctt     120
gtgggggtta cagctgcacg catggaactg agcttcttca aaagtgatca gtcatcaagt     180
tatgatgatg atgagtattc aaaaccatgc tgtgatctct gcatgtgcac acgctcaatg     240
cctcctcaat gcagctgtga agatattagg ctgaattcat gccactcaga ttgtaagagc     300
tgtatgtgca cacgctcaca gccaggacag tgtcgttgtc ttgacaccaa cgacttctgc     360
tacaaacctt gcaagtccag agatgactag atgaagccag tgctacttct tacactctcc     420
ttcctccccc tctttgcttt cttaactaac cttccattag ctttctcaaa tgaagttgaa     480
caagttgtgg ataccaaagg caagcccatt ttccctggtg ctacatacta cattatgcca     540
gcattatttg gggcagctgg tggtggagtg aaacttggca agactgcaaa ctcaaggtgc     600
ccagttactg ttttgcaaga cttttcagaa gtggttcgtg gtcttccagt gagattcaag     660
atacctggaa taagccctgg catcatcttt acaggtaccc cactggaaat tgagtttgca     720
tggaagccag ggtgtgctga atcctcgaaa tgggtggtgt ttgtggacaa tgaaattgaa     780
aaggcatgtg tgggaattgg tggtcctgaa gatcatccag ggcaacaaac ccgtagtggc     840
acattccaca ttgagaaata caattttgga tataagcttg tgttttgtat caatggctct     900
tccgtttgtt tggatattgg gaggtttgat gctaacaatg gtgagagtgg aagacggttg     960
aatctcactg agcatgaggc cttcgacctt                                      990

<210> SEQ ID NO 2
<211> LENGTH: 19
<212> TYPE: DNA
<213> ORGANISM: Artificial
<220> FEATURE:
<223> OTHER INFORMATION: Left Primer

<400> SEQUENCE: 2
caccatgagt ttgaagaac                                                   19

<210> SEQ ID NO 3
<211> LENGTH: 19
<212> TYPE: DNA
<213> ORGANISM: Artificial
<220> FEATURE:
<223> OTHER INFORMATION: Right Primer

<400> SEQUENCE: 3
```

```
gtcgactcaa actacagac                                             19

<210> SEQ ID NO 4
<211> LENGTH: 988
<212> TYPE: DNA
<213> ORGANISM: Mucuna pruriense

<400> SEQUENCE: 4
caccatgagt tgargaaca acatggtggt gctaaaggtg tgtttgttgc ttcttttcct   60
tgtgggggtt acagctgcac gcatggaact gagcttcttc aaaagtgatc agtcatcaag  120
ttatgatgat gatgagtatt caaaaccatg ctgtgatctc tgcatgtgca cacgctcaat  180
gcctcctcaa tgcagctgtg aagatattag gctgaattca tgccactcag attgtaagag  240
ctgtatgtgc acacgctcac agccaggaca gtgtcgttgt cttgacacca acgacttctg  300
ctacaaacct tgcaagtcca gagatgacta gatgaagcca gtgctacttc ttacactctc  360
cttcctcccc ctctttgctt tcttaactaa ccttccatta gctttctcaa atgaagttga  420
acaagttgtg gataccaaag gcaagcccat tttccctggt gctacatact acattatgcc  480
agcattattt ggggcagctg gtggtggagt gaaacttggc aagactgcaa actcaaggtg  540
cccagttact gttttgcaag acttttcaga agtggttcgt ggtcttccag tgagattcaa  600
gatacctgga ataagccctg gcatcatctt tacaggtacc ccactggaaa ttgagtttgc  660
atggaagcca gggtgtgctg aatcctcgaa atgggtggtg tttgtggaca atgaaattga  720
aaaggcatgt gtgggaattg gtggtcctga agatcatcca gggcaacaaa cccgtagtgg  780
cacattccac attgagaaat acaattttgg atataagctt gtgttttgta tcaatggctc  840
ttccgtttgt ttggatattg ggaggtttga tgctaacaat ggtgagagtg aagacggtt   900
gaatctcact gagcatgagg ccttcgacct tgttttcgta gaggcttctg actatgaaga  960
aataattaag tctgtagttt gagtcgac                                    988

<210> SEQ ID NO 5
<211> LENGTH: 324
<212> TYPE: DNA
<213> ORGANISM: Phaseolus acutifolius

<400> SEQUENCE: 5
atgatggtgc tgaaggtgtg tctgttacta gttttccttg caggggttac tactgctcgc   60
atggatctga accacctcat cagaagtaat catcatgact caagcgatga gccttctgag  120
tcttcagaac catgctgtga tcactgcata tgcacagctt caatacctcc tatatgccaa  180
tgcacagata ttaggttgaa ttcatgccac tcagcttgca aatcctgtat gtgtacgcga  240
tcaatgccag gcaagtgtcg ttgccttgac accactgatt tttgttacaa atcttgcaag  300
tccagtggtg aagatgatga ctga                                        324

<210> SEQ ID NO 6
<211> LENGTH: 324
<212> TYPE: DNA
<213> ORGANISM: Phaseolus grayanus

<400> SEQUENCE: 6
atgatggtgc tgaaggtgtg tttgttgcta gttttcttg taggggttac tactgctcgc    60
atggatctga accacctcat cagaggtaat catcatgact caagcgatga gccttctgag  120
tcttcagaac catgctgtga tctctgcgtg tgcacagatt caatacctcc tatatgccaa  180
tgcacagata ttaggttgaa ctcatgccac tcagcttgca aaacctgtat gtgtacacga  240
```

```
tcaatgccag gcaagtgtcg ttgccttgac accactgatt tttgttacaa atcttgcaag    300
tccagtggtg aagatgatga ctga                                           324
```

<210> SEQ ID NO 7
<211> LENGTH: 324
<212> TYPE: DNA
<213> ORGANISM: Phaseolus maculatus

<400> SEQUENCE: 7

```
atgatggtgc tgaaggtgtg tctgttacta gttttccttg caggggttac tactgctcgc     60
atggatctga accacctcat cagaagtaat catcatgact caagcgatga gccttctgag    120
tcttcagaac catgctgtga tctctgcttg tgcacagctt caatacctcc tatatgccaa    180
tgctcagata ttaggttgaa ttcgtgccac tcagcttgca aatcctgtat gtgtacacga    240
tcaatgccag gcaagtgtcg ttgccttgac accaccgatt tctgttacaa atcttgcaag    300
tccagtggtg aagatgatga ctga                                           324
```

<210> SEQ ID NO 8
<211> LENGTH: 60
<212> TYPE: DNA
<213> ORGANISM: Phaseolus microcarpus

<400> SEQUENCE: 8

```
tgtcgttgcc ttgacaccac cgatttctgt tacaaatctt gcaagtccag tggtgaagat     60
```

<210> SEQ ID NO 9
<211> LENGTH: 60
<212> TYPE: DNA
<213> ORGANISM: Glycine max

<400> SEQUENCE: 9

```
tgtcgttgcc ttgacaccac cgacttctgc tacaaacctt gcaagtccag tgatgaagat     60
```

<210> SEQ ID NO 10
<211> LENGTH: 62
<212> TYPE: DNA
<213> ORGANISM: Artificial
<220> FEATURE:
<223> OTHER INFORMATION: Predicted DNA sequence of Fig 7B

<400> SEQUENCE: 10

```
tgtcgttgcg ttgacaccac ctgatttttct gttacaaacc ttgcaagtcc ggtggtggag    60
at                                                                    62
```

<210> SEQ ID NO 11
<211> LENGTH: 20
<212> TYPE: PRT
<213> ORGANISM: Unknown
<220> FEATURE:
<223> OTHER INFORMATION: Consensus Protein Sequence of Fig. 7B

<400> SEQUENCE: 11

```
Cys Arg Cys Val Asp Thr Thr Asp Phe Cys Tyr Lys Pro Cys Lys Ser
1               5                   10                  15

Gly Gly Gly Asp
            20
```

-continued

```
<210> SEQ ID NO 12
<211> LENGTH: 8
<212> TYPE: PRT
<213> ORGANISM: Mucuna pruriense

<400> SEQUENCE: 12

Asp Asp Arg Glu Pro Val Asp Thr
1               5
```